(12) United States Patent
Schön

(10) Patent No.: US 7,285,249 B2
(45) Date of Patent: Oct. 23, 2007

(54) APPARATUS FOR THE PROVISION OF A BLOCK FLANGE OF A MANHOLE APERTURE OR THE LIKE, IN PARTICULAR FOR FLUIDIZED BED REACTORS

(75) Inventor: Hartmut Schön, Oberursel (DE)

(73) Assignee: Krupp Uhde GmbH, Dortmund (DE)

( * ) Notice: Subject to any disclaimer, the term of this patent is extended or adjusted under 35 U.S.C. 154(b) by 321 days.

(21) Appl. No.: 10/976,287

(22) Filed: Oct. 27, 2004

(65) Prior Publication Data

US 2005/0058580 A1  Mar. 17, 2005

Related U.S. Application Data

(63) Continuation of application No. PCT/EP99/08001, filed on Oct. 27, 1999.

(30) Foreign Application Priority Data

Nov. 7, 1998 (DE) ................................ 198 51 423

(51) Int. Cl.
 *B01D 3/32* (2006.01)
 *C10B 43/00* (2006.01)
 *B01J 19/00* (2006.01)
 *B01J 8/18* (2006.01)

(52) U.S. Cl. ...................... 422/139; 422/129; 202/239; 202/240; 202/241; 202/242; 202/250; 202/251; 202/262

(58) Field of Classification Search ................ 422/129; 202/239, 240, 241, 242, 250, 251, 262; 404/25
See application file for complete search history.

(56) References Cited

U.S. PATENT DOCUMENTS 4,203,686 A * 5/1980 Bowman ...................... 404/25
4,411,877 A * 10/1983 Notman ....................... 423/359

* cited by examiner

*Primary Examiner*—Glenn Caldarola
*Assistant Examiner*—Kaity Handal
(74) *Attorney, Agent, or Firm*—Katten Muchin Roseman LLP

(57) ABSTRACT

An apparatus for the provision of a block flange of a manhole aperture or the like, in particular for fluidized bed reactors for the oxychlorination of ethylene, oxygen and HCl, having a wall flange fixed in the reactor wall, is intended to provide a solution whereby all other auxiliary measures can be dispensed with and the expense associated therewith can be eliminated without the functionality of the system suffering as a result and without undesirable deposits being formed in these areas.

This is achieved in that the flange surface (5) pointing inward and downward in the direction of gravity is of beveled design, at least in some areas.

4 Claims, 2 Drawing Sheets

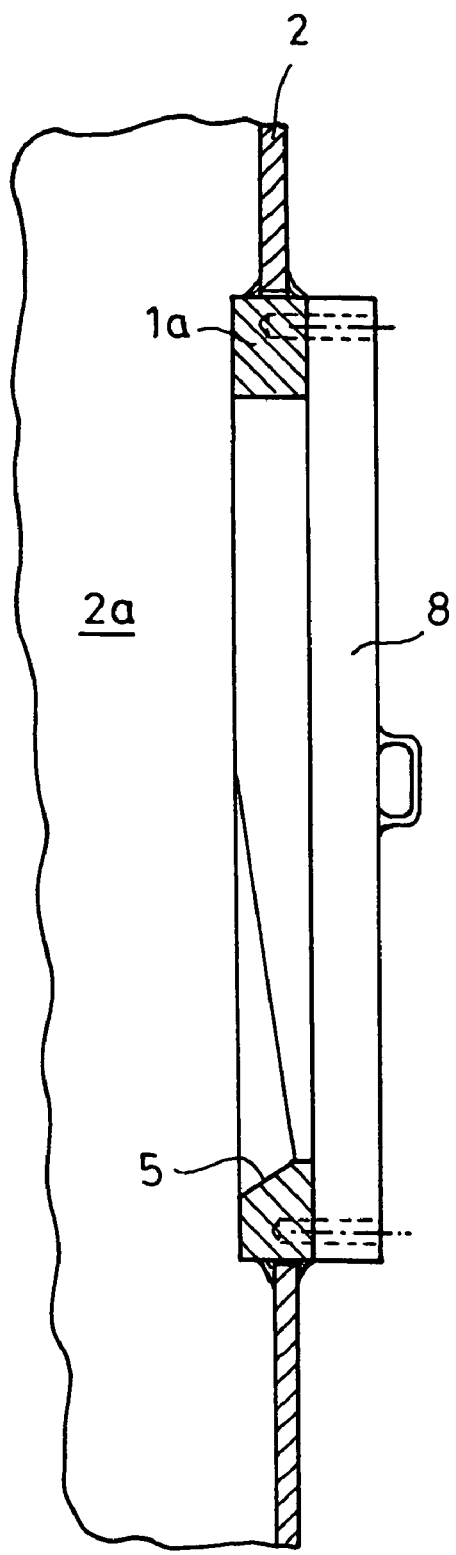
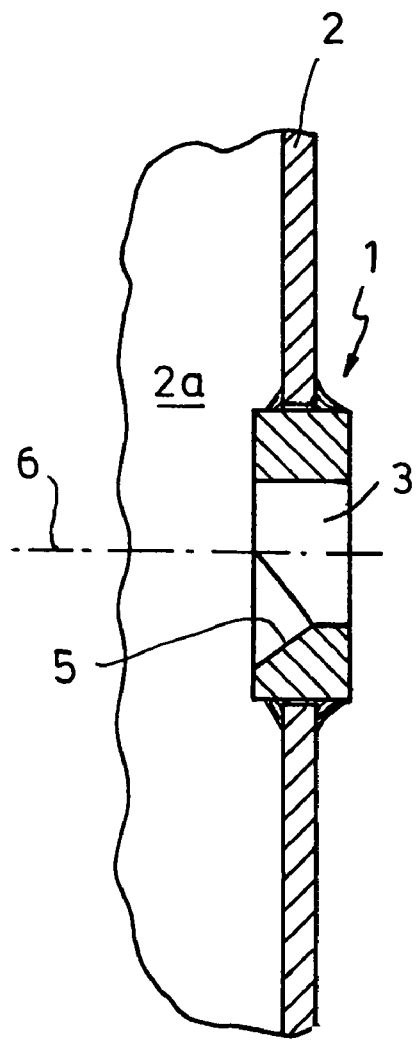
FIG. 2
FIG. 3

APPARATUS FOR THE PROVISION OF A BLOCK FLANGE OF A MANHOLE APERTURE OR THE LIKE, IN PARTICULAR FOR FLUIDIZED BED REACTORS

This application is a continuation of International Application No. PCT/EP99/08001, filed Oct. 27, 1999, which claims priority to German application number 198 51 423.9 filed on Nov. 7. 1998, and which is herein incorporated by reference.

FIELD OF DISCLOSURE

The invention relates to an apparatus for the provision of a block flange of a manhole aperture or the like, in particular for fluidized bed reactors for the oxychlorination of ethylene, oxygen and HCl, having a wall flange fixed in the reactor wall.

BACKGROUND OF THE DISCLOSURE

In what is known as oxychlorination, ethylene, oxygen and HCl are reacted in a fluidized bed reactor (oxyreactor) over a copper-containing catalyst to give 1,2-dichloroethane and water. In operation, and when the plant is shut down, catalyst deposits may occur in any dead spaces within the reactor. The presence of HCl results in the formation of hydrochloric acid when the temperature falls below the dew point, and hence causes severe corrosion. Particularly at risk here are dead spaces in the shell region, such as any manholes and measuring ports. Attempts have been made to remedy this disadvantage by, for example, providing heated flushing lines at all measuring ports, in order also to prevent adverse effects on measurements and temperatures falling below the dew point.

With manhole designs, it is known to equip the lids of said manholes internally with an additional displacement body which is so designed as to produce the smoothest possible flush transition to the inner surface of the reactor shell.

It is an object of the invention to provide a solution whereby all other auxiliary measures can be dispensed with and the expense associated therewith can be eliminated without the functionality of the system suffering as a result and without undesirable deposits being formed in these areas.

This object is achieved, according to the invention, with an apparatus of the type described initially in that the flange surface pointing inward and downward in the direction of gravity is of beveled design, at least in some areas.

The invention entails a number of advantages, for example in that possible dead spaces in which catalyst deposits may be formed are reduced and all heated flushing lines that are employed in the conventional solutions, with filter stations, flowmeters, condensate collectors, mountings and the like, are eliminated.

In an embodiment, it is envisaged that the surface bevel is so great, at least in its area that is lowest in the direction of gravity, that deposition of catalyst granules or the like is prevented.

It is particularly advantageous if, as the invention likewise envisages, the bevel of the surface is designed to increase, beginning from the horizontal median plane in the inner edge region toward the vertical center of the flange ring.

With this design, a smooth, homogeneous, funnel-like slide is formed, directed toward the interior of the reactor, so that, for example, when the reactor is switched off and the fluidized bed sinks, the deposition of catalyst material or the like is reliably prevented.

BRIEF DESCRIPTION OF THE DRAWINGS

Further features, details and advantages of the invention are apparent from the description that follows and from reference to the drawing, in which:

FIG. 2 shows a simplified sectional view of a manhole, and FIG. 3 shows a simplified sectional view of a block flange approximately in accordance with FIG. 1.

DESCRIPTION OF THE PREFERRED EMBODIMENT

Figure 1:
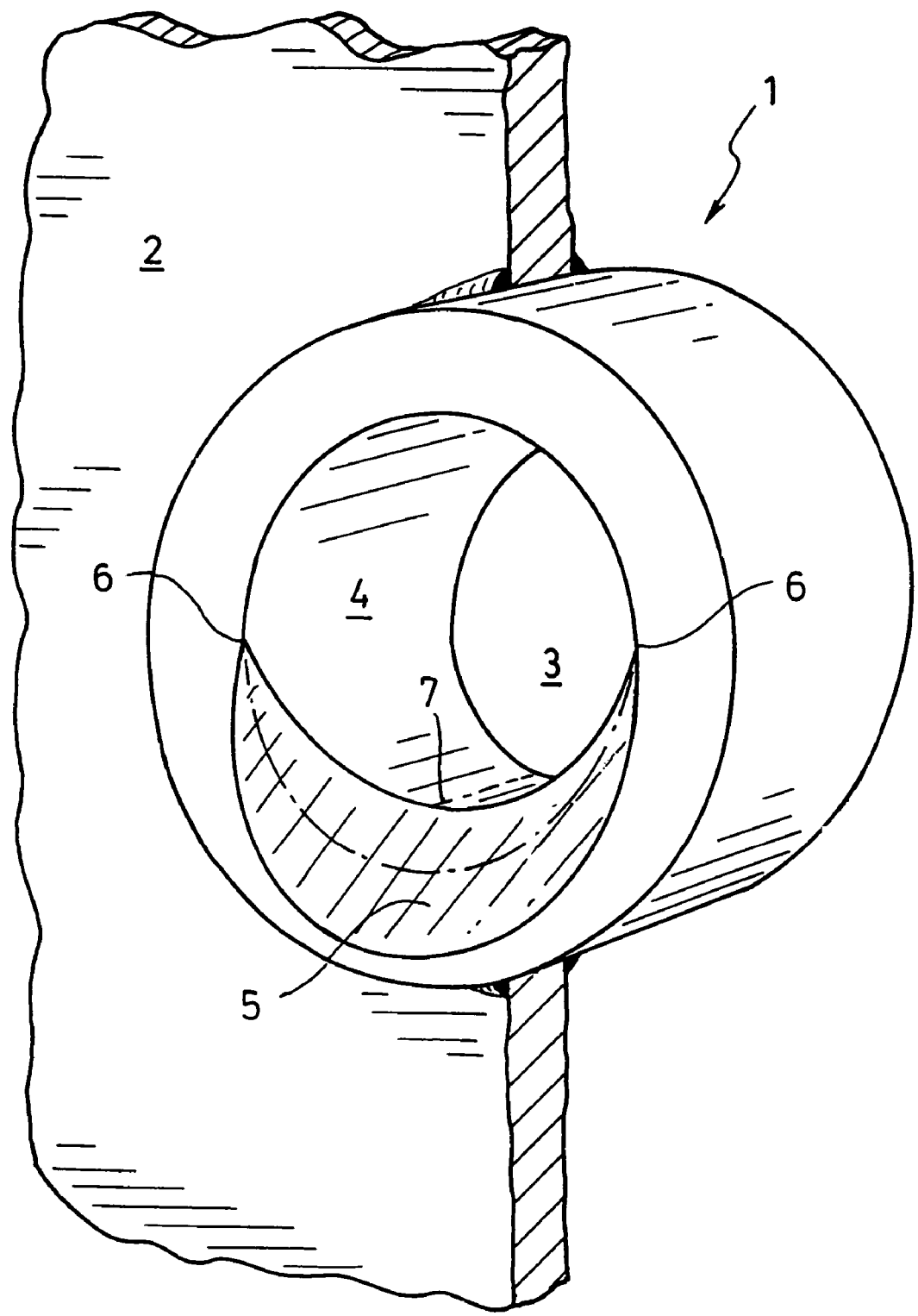
FIG. 1 shows a simplified perspective view of a block flange according to the invention.

Referring to FIG. 1, a block flange generally designated 1 according to the invention is welded into a reactor wall 2. The block flange has a certain cylindrical extent and has a passage aperture 3, for example for a measuring instrument, a probe or the like.

In its inward-pointing area, designated 2a in FIG. 2, the flange inner surface 4 is beveled, the bevel being designated 5 in FIG. 1. This beveled surface 5 begins approximately at the center horizontal line 6 of the flange 1, extends as far as the horizontal center, designated 7, of the flange and from there onward to the vertical center 6, so that a form of slide results. Material falling thereon is automatically rejected as a result of gravity.

FIG. 2 shows a manhole design, and here again a corresponding flange design is shown, the manhole being closed by a cover designated in this case 8.

FIG. 3 shows a block flange 1 of this type in section.

The examples of embodiment of the invention described can of course be modified in a great many respects without departing from the basic concept. Thus, the flange 1 or 1a can, in particular, be welded in flush with the inner wall surface of the reactor wall 2, the flange or flange bore 3 can be arranged at a slightly downward-pointing angle to assist the sliding-off of material falling thereon, and so on.

The invention claimed is:

1. A block flange for a manhole, the flange for mounting in an upright wall of a fluidized bed reactor, the flange comprising:

an inner flange surface having a beveled portion and an unbeveled portion on an inward side, the inward side being opposite to the closure, the beveled portion being beveled from an edge of the block flange on the inward side toward a center of the block flange, wherein when mounted in the wall of the reactor the beveled portion is disposed downward to prevent deposition of material on the inner flange surface.

2. The block flange of claim 1, wherein the beveled portion has a bevel angle sufficient for preventing deposition of catalyst granules.

3. The block flange of claim 1 further comprising a horizontal median plane and a vertical median plane and wherein the beveled portion increases from an edge of the block flange on the inward side toward a center of the block flange, where the horizontal medial plane intersects the vertical median plane.

4. A flange for a manhole, the flange for mounting in an upright wall of a fluidized bed reactor, the flange comprising:

an annulus for mounting into the wall, a beveled portion disposed in an interior surface of the annulus on an inward side, the inward side being opposite to the closure, wherein when mounted in the wall of the reactor the beveled portion is disposed downward to facilitate flow under gravity from the annulus.

* * * * *

UNITED STATES PATENT AND TRADEMARK OFFICE
CERTIFICATE OF CORRECTION

PATENT NO.         : 7,285,249 B2
APPLICATION NO.    : 10/976287
DATED              : October 23, 2007
INVENTOR(S)        : Hartmut Schön Page 1 of 1

It is certified that error appears in the above-identified patent and that said Letters Patent is hereby corrected as shown below:

On the Title Page

Assignee (Item 73) is incorrect. Item 73 is changed from Krupp Uhde GmbH, Dortmund (DE)

to UHDE GmbH, Dortmund (DE).

Signed and Sealed this

Fifteenth Day of April, 2008

JON W. DUDAS
*Director of the United States Patent and Trademark Office*